(12) United States Patent
Al-Ajaji

(10) Patent No.: US 11,714,077 B1
(45) Date of Patent: Aug. 1, 2023

(54) SELF DEPLOYABLE AND RETRIEVABLE APPARATUS FOR FACILITATING DATA COLLECTION FROM MULTIPLE DEPTHS OF WATER BODIES

(71) Applicant: Abdulaziz Al-Ajaji, Al Khobar (SA)

(72) Inventor: Abdulaziz Al-Ajaji, Al Khobar (SA)

( * ) Notice: Subject to any disclaimer, the term of this patent is extended or adjusted under 35 U.S.C. 154(b) by 0 days.

(21) Appl. No.: 17/928,281

(22) PCT Filed: Jul. 25, 2022

(86) PCT No.: PCT/IB2022/056831
§ 371 (c)(1),
(2) Date: Jan. 25, 2023

(51) Int. Cl.
| | | |
|---|---|---|
| *G01N 33/18* | (2006.01) |
| *G01C 13/00* | (2006.01) |
| *B63B 22/12* | (2006.01) |
| *B63B 22/18* | (2006.01) |
| *B63B 22/20* | (2006.01) |
| *B63B 22/00* | (2006.01) |

(52) U.S. Cl.
CPC ......... *G01N 33/1886* (2013.01); *B63B 22/12* (2013.01); *B63B 22/18* (2013.01); *B63B 22/20* (2013.01); *G01C 13/00* (2013.01); *G01N 33/18* (2013.01); *B63B 2022/006* (2013.01); *B63B 2207/02* (2013.01); *B63B 2211/02* (2013.01)

(58) Field of Classification Search
CPC ......... B63B 22/12; B63B 22/18; B63B 22/20; B63B 22/22; B63B 2022/006; B63B 2203/00; B63B 2207/02; B63B 2211/02; B63G 8/22; G01C 13/00; G01C 13/002; G01C 13/004; G01C 13/006; G01C 13/008; G01N 33/18; G01N 33/1806; G01N 33/1886
See application file for complete search history.

(56) References Cited

U.S. PATENT DOCUMENTS

| | | | | |
|---|---|---|---|---|
| 4,202,036 | A * | 5/1980 | Bowditch | B63C 11/36 702/33 |
| 5,303,552 | A * | 4/1994 | Webb | B63B 22/22 114/331 |
| 9,563,203 | B2 * | 2/2017 | Davoodi | B63G 8/001 |
| 10,006,897 | B1 * | 6/2018 | Ensign | G01N 33/18 |
| 10,518,848 | B2 * | 12/2019 | Sinclair | A01K 63/00 |
| 11,560,204 | B2 * | 1/2023 | Cardenas | B63B 22/20 |
| 2021/0061488 | A1 * | 3/2021 | Smithers | C01B 3/06 |

* cited by examiner

*Primary Examiner* — Ajay Vasudeva
(74) *Attorney, Agent, or Firm* — Dhiraj Jindal; Patent Yogi LLC

(57) ABSTRACT

A self-deployable apparatus for facilitating collecting data from multiple depths of water bodies. Further, the self deployable apparatus comprises a main body, substances, a sensor, a storage device, and a power source. Further, the substances in amounts are to be disposed in a second interior space of the main body for sinking the self-deployable apparatus to a depth of water body. Further, the amounts of the substances undergo a thermochemical reaction at a temperature for producing a gaseous substance. Further, a check valve of the main body expels a portion of the gaseous substance from the second interior space for rising the self-deployable apparatus to a surface of the water body. Further, the sensor generates sensor data based on detecting a parameter of a water sample. Further, the storage device stores the sensor data. Further, the power source powers the sensor and the storage device.

20 Claims, 10 Drawing Sheets

SELF DEPLOYABLE AND RETRIEVABLE APPARATUS FOR FACILITATING DATA COLLECTION FROM MULTIPLE DEPTHS OF WATER BODIES

FIELD OF THE INVENTION

Generally, the present disclosure relates to the field of measuring and testing. More specifically, the present disclosure relates to a self deployable and retrievable apparatus for facilitating data collection from multiple depths of water bodies.

BACKGROUND OF THE INVENTION

The field of measuring and testing is technologically important to several industries, business organizations, and/or individuals. In particular, the use of an apparatus and a device are prevalent for measuring parameters of water samples at multiple depths of water bodies to collect data of the water samples.

Existing apparatuses for collecting data from multiple depths of water bodies are deficient with regard to several aspects. For instance, current apparatuses are clunky and heavy weighted. Furthermore, current apparatuses require a rig for lowering the current apparatuses at multiple depths of water bodies and recovering current apparatuses from the multiple depths. Moreover, current apparatuses are not easy to assemble and disassemble.

Therefore, there is a need for a self deployable and retrievable apparatus for facilitating data collection from multiple depths of water bodies that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a self deployable apparatus for facilitating collecting data from multiple depths of water bodies, in accordance with some embodiments. Further, the self deployable apparatus may include a main body, at least two substances, at least one sensor, a storage device, and at least one power source. Further, the main body may include a first body portion and a second body portion. Further, the first body portion may include a first interior space and the second body portion may include a second interior space. Further, the first interior space may be fluidly isolated from the second interior space. Further, the second body portion may include a check valve. Further, the at least two substances in at least two amounts may be disposed in the second interior space. Further, the at least two amounts of the at least two substances add at least one weight to the main body for sinking the self deployable apparatus to at least one depth of at least one water body. Further, the at least two amounts of the at least two substances may be configured for undergoing a thermochemical reaction at a temperature for producing at least one gaseous substance in at least one amount. Further, the at least two amounts of the at least two substances achieve the temperature based on the sinking of the self deployable apparatus to the at least one depth of the at least one water body. Further, the at least one amount of the at least one gaseous substance exerts at least one pressure on the check valve. Further, the check valve may be configured for expelling at least one portion of the at least one amount of the at least one gaseous substance from the second interior space based on the at least one pressure exerted on the check valve. Further, the expelling of the at least one portion of the at least one amount of the at least one gaseous substance from the second interior space corresponds to removing at least one portion of the at least one weight from the main body. Further, the removing of the at least one portion of the at least one weight rises the self deployable apparatus to a surface of the at least one water body. Further, the at least one sensor may be attached to the first body portion. Further, the at least one sensor may be configured for generating at least one sensor data based on detecting at least one parameter of at least one water sample in the at least one depth of the at least one water body. Further, the storage device may be disposed in the first interior space. Further, the storage device may be communicatively coupled with the at least one sensor. Further, the storage device may be configured for storing the at least one sensor data. Further, the at least one power source may be disposed in the first interior space. Further, the at least one power source may be electrically coupled with the at least one sensor and the storage device. Further, the at least one power source may be configured for powering the at least one sensor and the storage device.

Further disclosed herein is a self deployable apparatus for facilitating collecting data from multiple depths of water bodies, in accordance with some embodiments. Further, the self deployable apparatus may include a main body, at least two substances, at least one sensor, a storage device, a communication interface, and at least one power source. Further, the main body may include a first body portion and a second body portion. Further, the first body portion may include a first interior space and the second body portion may include a second interior space. Further, the first interior space may be fluidly isolated from the second interior space. Further, the second body portion may include a check valve. Further, the at least two substances in at least two amounts may be disposed in the second interior space. Further, the at least two amounts of the at least two substances add at least one weight to the main body for sinking the self deployable apparatus to at least one depth of at least one water body. Further, the at least two amounts of the at least two substances may be configured for undergoing a thermochemical reaction at a temperature for producing at least one gaseous substance in at least one amount. Further, the at least two amounts of the at least two substances achieve the temperature based on the sinking of the self deployable apparatus to the at least one depth of the at least one water body. Further, the at least one amount of the at least one gaseous substance exerts at least one pressure on the check valve. Further, the check valve may be configured for expelling at least one portion of the at least one amount of the at least one gaseous substance from the second interior space based on the at least one pressure exerted on the check valve. Further, the expelling of the at least one portion of the at least one amount of the at least one gaseous substance from the second interior space corresponds to removing at least one portion of the at least one weight from the main body. Further, the removing of the at least one portion of the at least one weight rises the self deployable apparatus to a surface of the at least one water body. Further, the at least one sensor may be attached to the first body portion. Further, the at least one sensor may be configured for generating at least one sensor data based on detecting at least one parameter of at least one water sample in the at least one depth of the at least one water body. Further, the storage device may be disposed in the first interior space. Further, the storage device may be communicatively coupled with the at least one sensor. Further, the storage device may be configured for storing the at least one sensor data. Further, the communication interface may be disposed in the first interior space. Further, the communication interface may be communicatively coupled with the storage device. Further, the communication interface may be configured for transmitting the at least one sensor data to at least one device. Further, the at least one power source may be disposed in the first interior space. Further, the at least one power source may be electrically coupled with the at least one sensor, the storage device, and the communication interface. Further, the at least one power source may be configured for powering the at least one sensor, the storage device, and the communication interface.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

Figure 1:
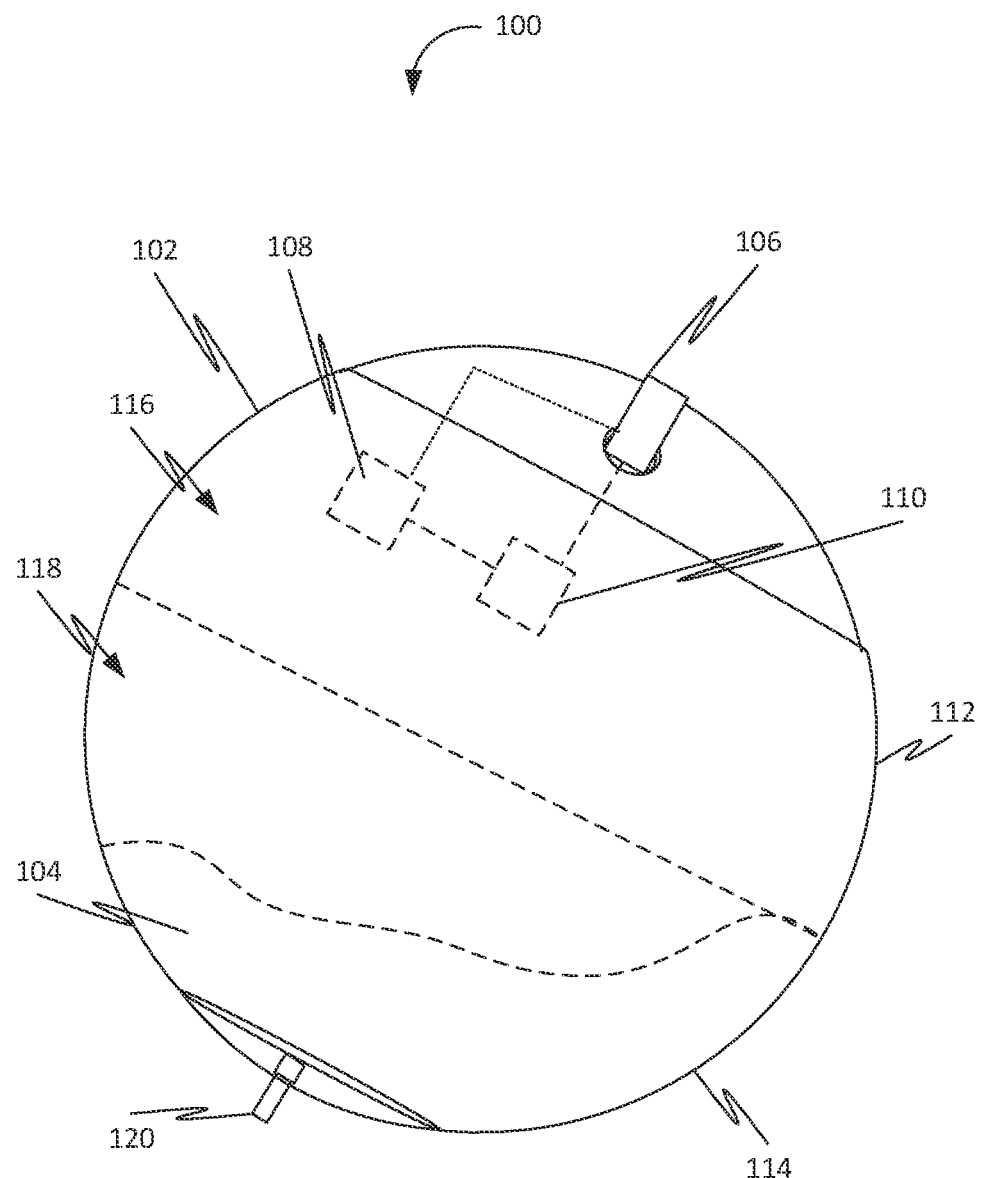
FIG. 1 is a front view of a self deployable apparatus for facilitating collecting data from multiple depths of water bodies, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of a self deployable apparatus for facilitating collecting data from multiple depths of water bodies, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smartphone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, a public database, a private database, and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled, and/or terminated based on a control input received from one or more devices operated by one or more users such as, for example, but not limited to, an end user, an admin, a service provider, a service consumer, an agent, a broker and a representative thereof. Further, the user as defined herein may refer to a human. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer, etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera, and so on. Likewise, the one or more steps may include receiving, using the communication device, the one or more embodied characteristics from one or more biometric sensors.

Further, one or more steps of the method may be automatically initiated, maintained, and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device, etc.) corresponding to the performance of the one or more steps, environmental variables (e.g. temperature, humidity, pressure, wind speed, lighting, sound, etc.) associated with a device corresponding to the performance of the one or more steps, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor, etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data, and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes a self deployable apparatus for facilitating collecting data from multiple depths of water bodies.

Further, the self deployable apparatus may be a SPHERICA. Further, the SPHERICA is a compact, self-deploying, and self-retrieving sensing platform for bottom hole pressure and temperature data monitoring and analysis. It houses a pressure and temperature sensor connected to an electronic circuit for data logging, as well as a thermochemical that can react at a certain temperature and escape the ball, making it light enough to float back to the surface.

Further, the SPHERICA's primary goal is well logging operations. It can also be used for Reservoir data monitoring (Pressure & Temperature), pressure build-up surveys, gradient surveys, and perforation efficiency monitoring.

Further, the SPHERICA aims to replace conventional wireline well logging tools that require lots of heavy equipment and manpower, are very costly and large in size, and need the well to be shut down during operation.

Further, the SPHERICA achieves this by replacing the wireline with a change in buoyancy that is achieved using a chemical reaction. The ball's density is less than that of water when it is empty (without chemicals). When chemicals are added, the weight increases making the density of the ball greater than water's, which allows the ball to sink. Once the SPHERICA reaches a certain depth, the outer temperature (which can reach up to 200 F) triggers the reaction of the chemicals which are converted to gas and can build up enough pressure inside the ball that allows them to be released into the well. Once the chemicals are ejected, the ball starts floating back up to the surface.

Further, the SPHERICA may include three main parts a main body, a top insert, and a bottom insert. Further, the main body may be 3D printed using PEEK HP3 material. Further, the main body may include two compartments. Further, the two compartments may include an upper compartment for SPHERICA electronics and a lower compartment for chemicals. Further, the top insert is made of Aluminium 7075-T6 and attached to the main body using 3 bolts. Further, the top insert may include a threaded hole for the sensor. Further, the bottom insert is made of Aluminium 7075-T6 and attached to the main body using 3 bolts. Further, the bottom insert may include a check valve (LEE COMPANY CKFA0936015A) to allow chemicals to exit the ball. Further, the main body may withstand pressures up to 4000 PSI at 248 F. Further, the SPHERICA electronics may include the sensor (BOSCH PST-F 2) to measure pressure from 0 to 280 bar and temperature from −40 to 140 C. Further, the SPHERICA electronics may include a custom made PCB. Further, the custom made PCB may operate at temperatures up to 120 C, store up to 32,000 records, and provide a battery life of up to 13 hours. Further, the chemicals used are Ammonium Chloride ($NH_4Cl$) and Sodium Nitrite ($NaNO_2$). Both are mixed in a water solution with certain molarity. The molarity controls the trigger temperature and max pressure yielded by the reaction.

Further, the SPHERICA may be a small and light-weight sphere with various sizes to safely go through different tubing sizes. Further, the SPHERICA does not require a rig-up, a rig down, or heavy equipment. Further, the SPHERICA may be easy to assemble and disassemble. Further, the SPHERICA may be suitable for multi-run applications.

Further, the SPHERICA uses the thermochemical reaction to replace the wireline technology. Further, the SPHERICA uses compact sensors and custom-made PCBs to read the sensors and store the data instead of sending it directly to the surface. Further, the SPHERICA is of a spherical shape which minimizes the chances of the SPHERICA getting stuck in the well.

FIG. 1 is a front view of a self deployable apparatus 100 for facilitating collecting data from multiple depths of water bodies, in accordance with some embodiments. Further, the self deployable apparatus 100 may include a main body 102, at least two substances 104, at least one sensor 106, a storage device 108, and at least one power source 110.

Further, the main body 102 may include a first body portion 112 and a second body portion 114. Further, the first body portion 112 may include a first interior space 116 and the second body portion 114 may include a second interior space 118. Further, the first interior space 116 may be fluidly isolated from the second interior space 118. Further, the second body portion 114 may include a check valve 120. Further, the main body 102 may be 3D printed using PEEK HP3 material. Further, the first body portion 112 may be an upper compartment of the main body 102 and the second body portion 114 may be a lower compartment.

Further, the at least two substances 104 in at least two amounts may be disposed in the second interior space 118. Further, the at least two amounts of the at least two substances 104 add at least one weight to the main body 102 for sinking the self deployable apparatus 100 to at least one depth of at least one water body. Further, the at least two amounts of the at least two substances 104 may be configured for undergoing a thermochemical reaction at a temperature for producing at least one gaseous substance in at least one amount. Further, the at least two amounts of the at least two substances 104 achieve the temperature based on the sinking of the self deployable apparatus 100 to the at least one depth of the at least one water body. Further, the at least one amount of the at least one gaseous substance exerts at least one pressure on the check valve 120. Further, the check valve 120 may be configured for expelling at least one portion of the at least one amount of the at least one gaseous substance from the second interior space 118 based on the at least one pressure exerted on the check valve 120. Further, the expelling of the at least one portion of the at least one amount of the at least one gaseous substance from the second interior space 118 corresponds to removing at least one portion of the at least one weight from the main body 102. Further, the removing of the at least one portion of the at least one weight rises the self deployable apparatus 100 to a surface of the at least one water body.

Further, the at least one sensor 106 may be attached to the first body portion 112. Further, the at least one sensor 106 may be configured for generating at least one sensor data based on detecting at least one parameter of at least one water sample in the at least one depth of the at least one water body. Further, the at least one parameter may include a physio-chemical parameter of the at least one water sample. Further, the physio-chemical parameter may include a temperature, a pressure, a salinity, a conductivity, a pH, a turbidity, a total dissolved solids, a total suspended solids, an alkalinity, a biological oxygen demand, a chemical oxygen demand, a dissolved oxygen, a total organic carbon, a sulphate, a nitrate, a phosphate, etc. of the at least one water sample.

Further, the storage device 108 may be disposed in the first interior space 116. Further, the storage device 108 may be communicatively coupled with the at least one sensor 106. Further, the storage device 108 may be configured for storing the at least one sensor data.

Further, the at least one power source 110 may be disposed in the first interior space 116. Further, the at least one power source 110 may be electrically coupled with the at least one sensor 106 and the storage device 108. Further, the at least one power source 110 may be configured for powering the at least one sensor 106 and the storage device 108. Further, the at least one power source 110 may include at least one battery, at least one rechargeable battery, etc.

Further, in some embodiments, the main body 102 may be spherically shaped.

Further, in some embodiments, the main body 102 may be comprised of at least one material. Further, the at least one material may include PEEK HP3 material. Further, the at least one material makes the main body 102 lighter than water allowing the main body 102 to float on the surface of the at least one water body. Further, disposing of the at least two amounts of the at least two substances 104 in the second interior space 118 makes the main body 102 denser than the water allowing the main body 102 to sink in the at least one water body.

Further, in some embodiments, the at least two substances 104 comprise at least two aqueous solutions of at least two reactants. Further, the at least two aqueous solutions of the at least two reactants may be associated with at least two concentrations. Further, the at least two concentrations correspond to the temperature for the thermochemical reaction of the at least two amounts of the at least two substances 104. Further, the temperature corresponds to the sinking of the self deployable apparatus 100 to the at least one depth. Further, the at least two concentrations correspond to the sinking of the self deployable apparatus 100 to the at least one depth.

Figure 2:
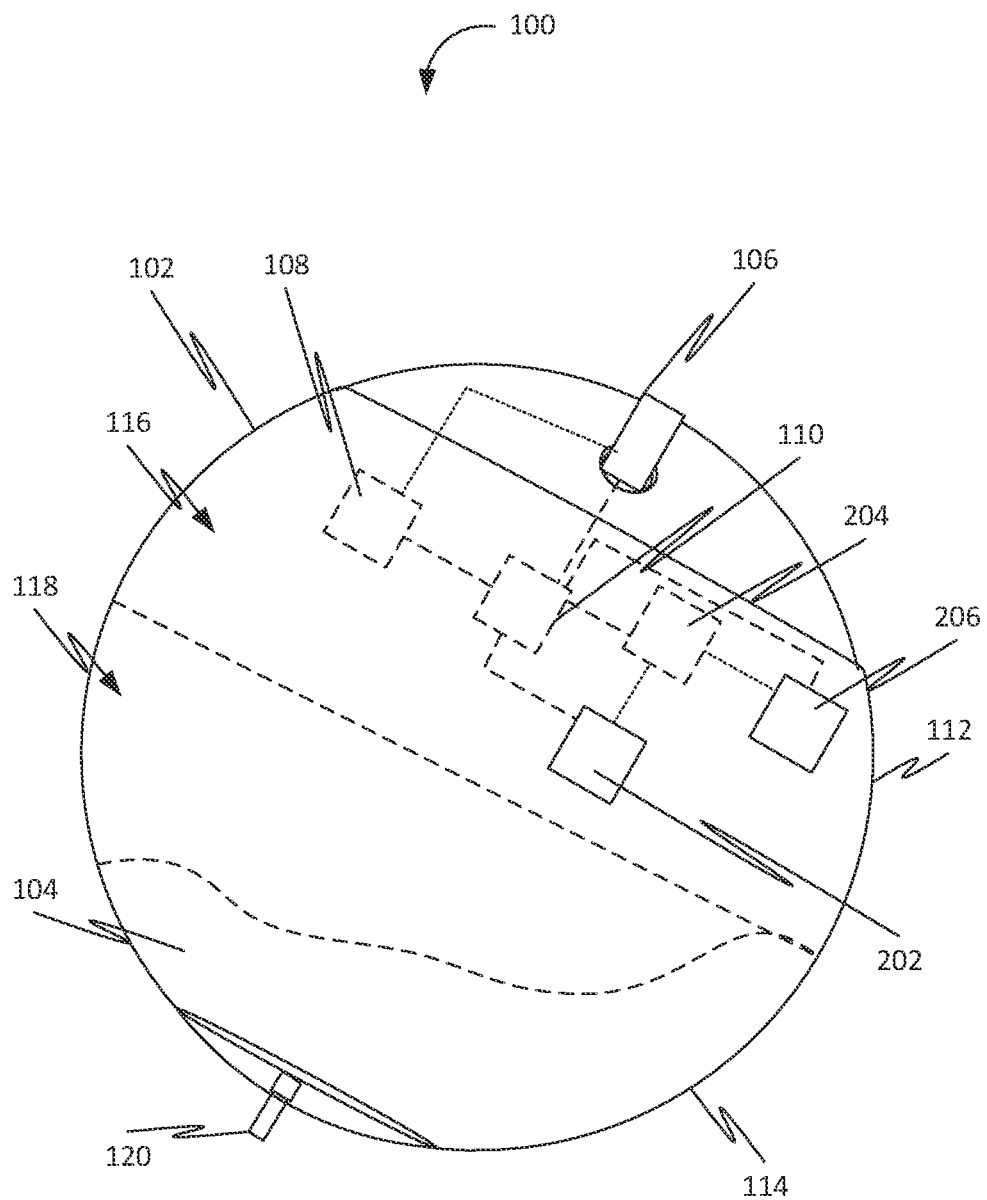
FIG. 2 is a front view of the self deployable apparatus, in accordance with some embodiments.

In further embodiments, the self deployable apparatus 100 may include at least one input device 202, a processing device 204, and at least one output device 206, as shown in FIG. 2. Further, the at least one input device 202 may be disposed on the main body 102. Further, the at least one input device 202 may be configured for receiving at least one depth indication for deploying the self deployable apparatus 100 to the at least one depth. Further, the processing device 204 may be disposed in the first interior space 116. Further, the processing device 204 may be communicatively coupled with the at least one input device 202. Further, the processing device 204 may be configured for analyzing the at least one depth indication. Further, the processing device 204 may be configured for determining the at least two concentrations of the at least two reactants based on the analyzing. Further, the at least two concentrations of the at least two reactants may be determined before disposing of the at least two substances 104 in the at least two amounts in the second interior space 118. Further, the processing device 204 may be configured for generating at least one indication of the at least two concentrations of the at least two reactants based on the determining. Further, the at least one output device 206 may be disposed on the main body 102. Further, the at least one output device 206 may be communicatively coupled with the processing device 204. Further, the at least one output device 206 may be configured for outputting the at least one indication of the at least two concentrations of the at least two reactants. Further, the at least one power source 110 may be electrically coupled with the at least one input device 202, the processing device 204, and the at least one output device 206. Further, the at least one power source 110 may be further configured for powering the at least one input device 202, the processing device 204, and the at least one output device 206.

In further embodiments, the self deployable apparatus 100 may include at least one heating device. Further, the at least one heating device may be disposed in the second interior space 118. Further, the at least one heating device may be communicatively coupled with the at least one sensor 106. Further, the at least one heating device may be configured for heating the at least two amounts of the at least two substances 104 based on the sinking of the self deployable apparatus 100 to the at least one depth of the at least one water body. Further, the at least two amounts of the at least two substances 104 achieve the temperature based on the heating of the at least two amounts of the at least two substances 104.

Further, in some embodiments, the at least two substances 104 comprise at least two aqueous solutions of at least two reactants. Further, the at least two aqueous solutions of the at least two reactants may be associated with at least two concentrations. Further, the at least two concentrations correspond the at least one amount of the at least gaseous substance.

Further, in some embodiments, the at least two substances 104 comprise Ammonium Chloride and Sodium Nitrite. Further, the at least one gaseous substance may include nitrogen gas.

Figure 3:
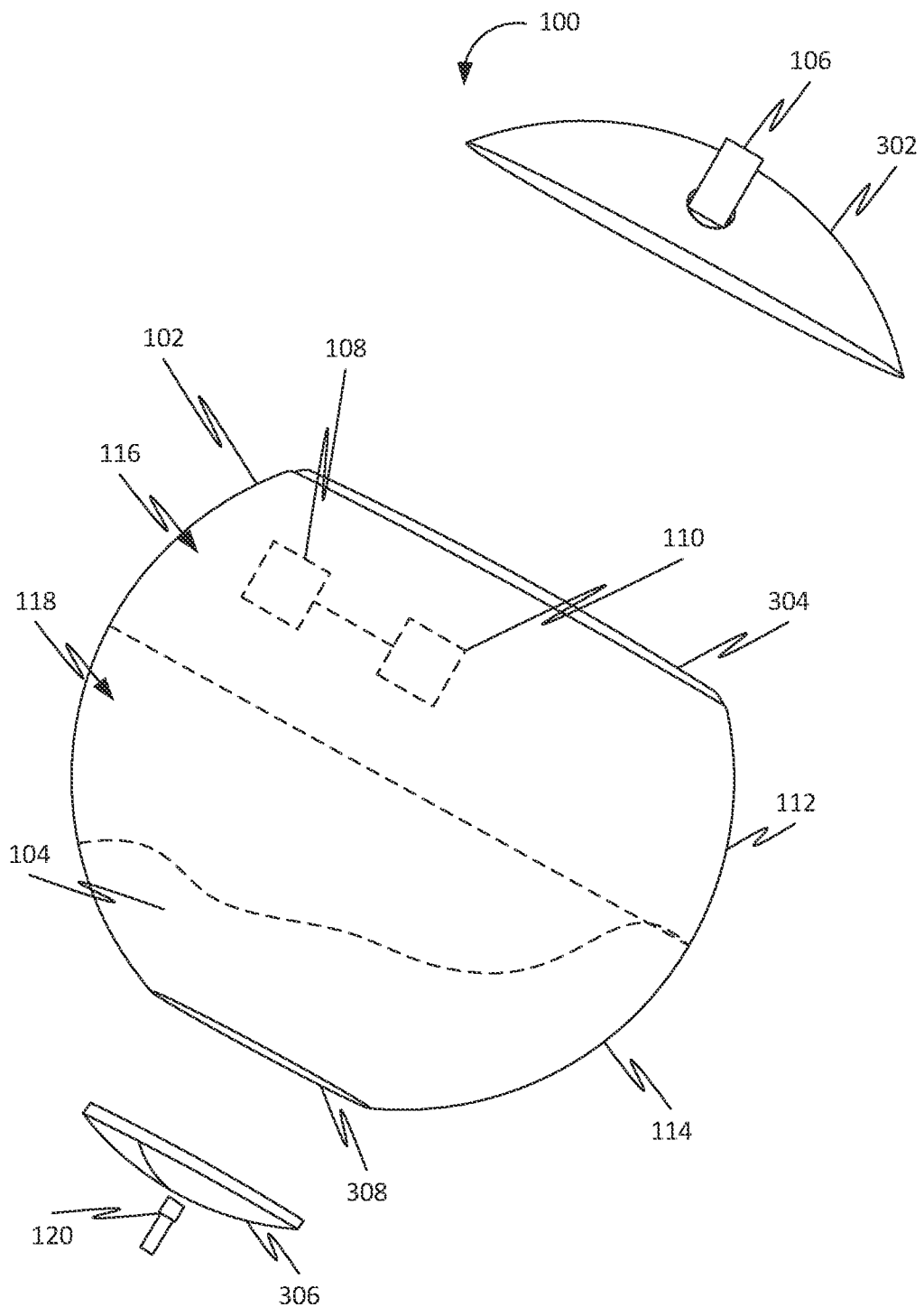
FIG. 3 is an exploded view of the self deployable apparatus, in accordance with some embodiments.

Further, in some embodiments, the second body portion 114 may include a second opening 308, as shown in FIG. 3, leading into the second interior space 118 and a second cover 306, as shown in FIG. 3, removably coupled with the second opening 308. Further, the second cover 306 transitions the second opening 308 between a closed state and at least one open state. Further, the second cover 306 fluidly seals the second body portion 114 in the closed state. Further, the at least two amounts of the at least two substances 104 may be to be disposed in the second interior space 118 through the second opening 308 in the at least one open state. Further, the second cover 306 may include a bottom insert.

Further, in some embodiments, the first body portion 112 may include a first opening 304, as shown in FIG. 3, leading into the first interior space 116 and a first cover 302, as shown in FIG. 3, removably coupled with the first opening 304. Further, the first cover 302 transitions the first opening 304 between a closed state and at least one open state. Further, the first cover 302 fluidly seals the second body portion 114 in the closed state. Further, at least one of the storage device 108 and the at least one power source 110 may be disposed in the first interior space 116 through the first opening 304 in the at least one open state. Further, the first cover 302 may include a top insert.

Figure 4:
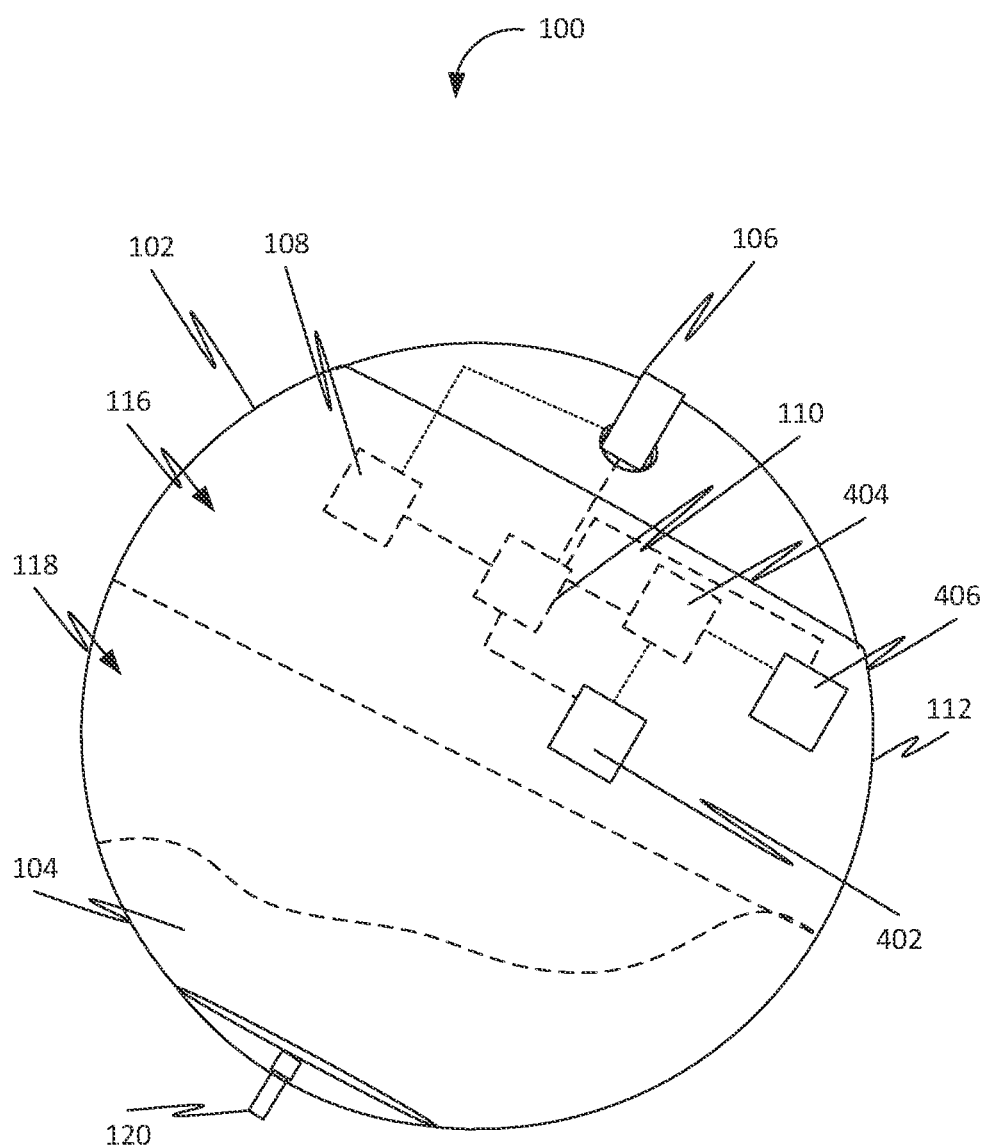
FIG. 4 is a front view of the self deployable apparatus, in accordance with some embodiments.

In further embodiments, the self deployable apparatus 100 may include at least one input device 402, a processing device 404, and at least one output device 406, as shown in FIG. 4. Further, the at least one input device 402 may be disposed on the main body 102. Further, the at least one input device 402 may be configured for receiving at least one depth indication for deploying the self deployable apparatus 100 to the at least one depth. Further, the processing device 404 may be disposed in the first interior space 116. Further, the processing device 404 may be communicatively coupled with the at least one input device 402. Further, the processing device 404 may be configured for analyzing the at least one depth indication. Further, the processing device 404 may be configured for determining the at least two amounts of the at least two substances 104 based on the analyzing. Further, the at least two amounts of the at least two substances 104 may be determined before disposing of the at least two substances 104 in the at least two amounts in the second interior space 118. Further, the processing device 404 may be configured for generating at least one indication of the at least two amounts of the at least two substances 104 based on the determining. Further, the at least one output device 406 may be disposed on the main body 102. Further, the at least one output device 406 may be communicatively coupled with the processing device 404. Further, the at least one output device 406 may be configured for outputting the at least one indication of the at least two amounts of the at least two substances 104. Further, the at least one power source 110 may be electrically coupled with the at least one input device 402, the processing device 404, and the at least one output device 406. Further, the at least one power source 110 may be further configured for powering the at least one input device 402, the processing device 404, and the at least one output device 406.

Figure 5:
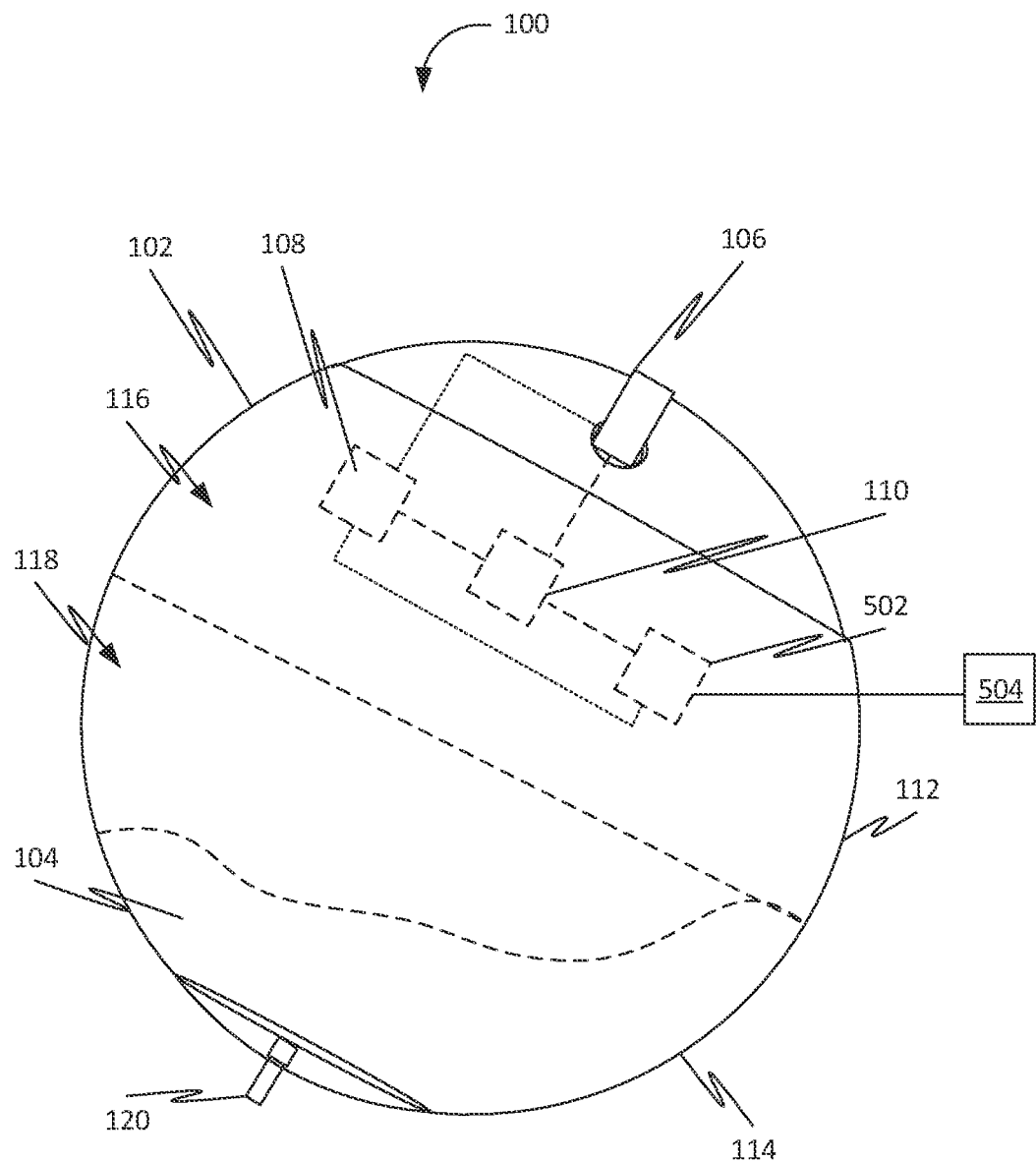
FIG. 5 is a front view of the self deployable apparatus, in accordance with some embodiments.

In further embodiments, the self deployable apparatus 100 may include a communication interface 502, as shown in FIG. 5. Further, the communication interface 502 may be disposed in the first interior space 116. Further, the communication interface 502 may be communicatively coupled with the storage device 108. Further, the communication interface 502 may be configured for transmitting the at least one sensor data to at least one device 504, as shown in FIG. 5. Further, the at least one power source 110 may be electrically coupled with the communication interface 502. Further, the at least one power source 110 may be configured for powering the communication interface 502. Further, the at least one device 504 may include a computing device, a client device, etc.

FIG. 2 is a front view of the self deployable apparatus 100, in accordance with some embodiments.

FIG. 3 is an exploded view of the self deployable apparatus 100, in accordance with some embodiments.

FIG. 4 is a front view of the self deployable apparatus 100, in accordance with some embodiments.

FIG. 5 is a front view of the self deployable apparatus 100, in accordance with some embodiments.

Figure 6:
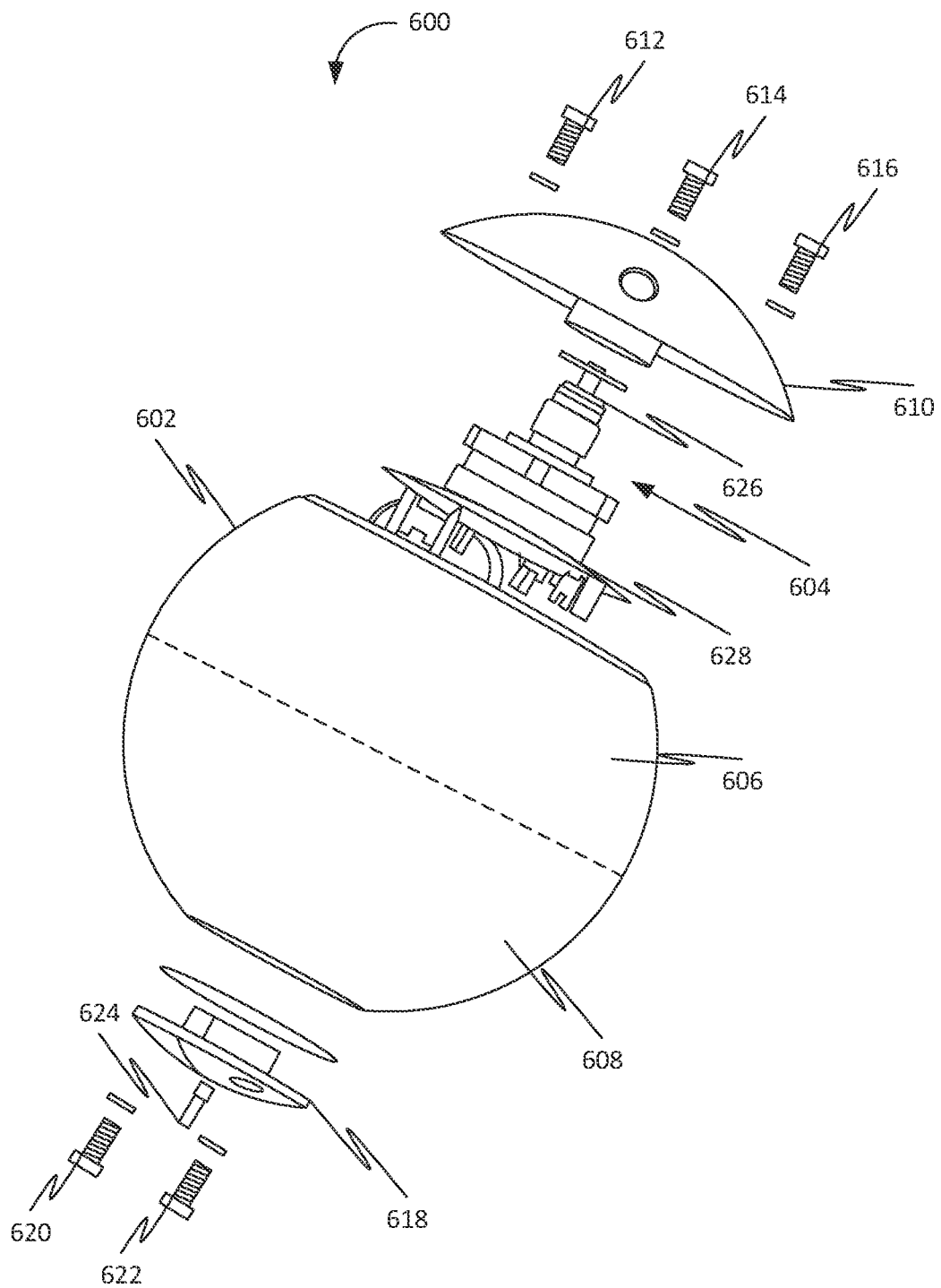
FIG. 6 is an exploded view of a self deployable apparatus for facilitating collecting data from multiple depths of water bodies, in accordance with some embodiments.

FIG. 6 is an exploded view of a self deployable apparatus 600 for facilitating collecting data from multiple depths of water bodies, in accordance with some embodiments. Further, the self deployable apparatus 600 may include a main body 602 and at least one electronic component 604. Further, the main body 602 may include an upper compartment 606 and a lower compartment 608. Further, the upper compartment 606 may include the at least one electronic component 604 and the lower compartment 608 may include chemicals. Further, the self deployable apparatus 600 may include a top insert 610 configured to be attached to the main body 602 using at least one first bolt 612-616. Further, the self deployable apparatus 600 may include a bottom insert 618 configured to be attached to the main body 602 using at least one second bolt 620-622. Further, the bottom insert 618 may include a check valve 624. Further, the check valve 624 may allow the chemicals to escape from the lower compartment 608. Further, the at least one electronic component 604 may include at least one sensor 626 and a custom made PCB 628.

Figure 7:
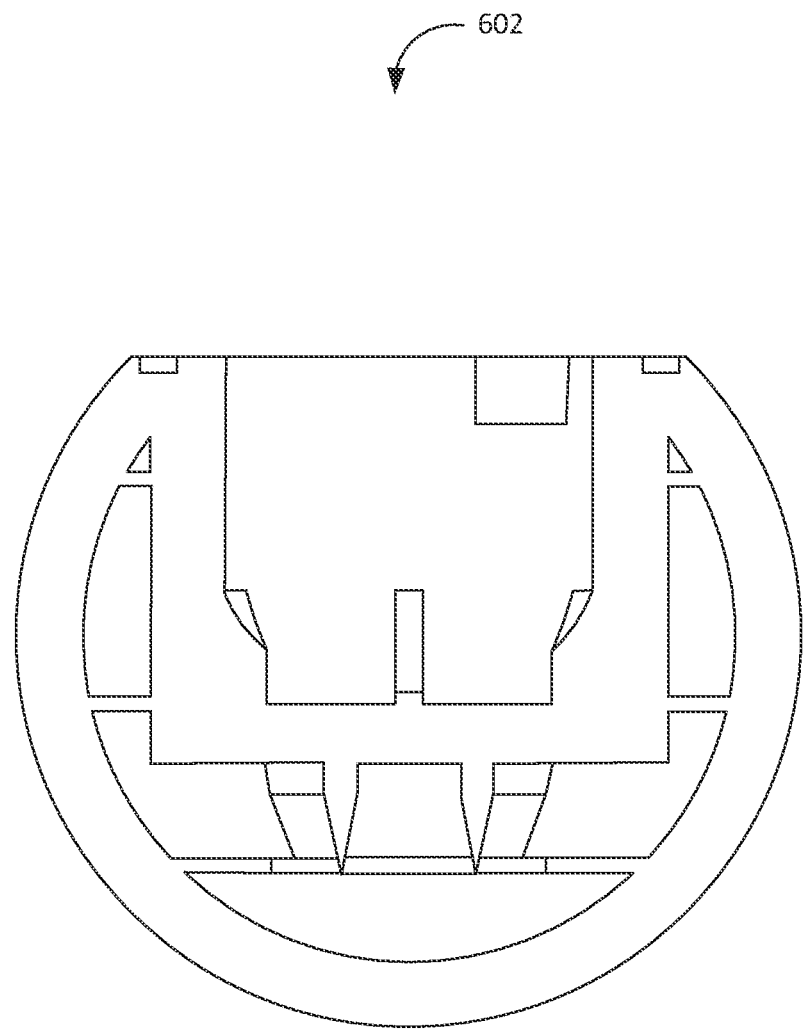
FIG. 7 is a cross sectional view of the main body of the self deployable apparatus, in accordance with some embodiments.

FIG. 7 is a cross sectional view of the main body 602 of the self deployable apparatus 600, in accordance with some embodiments.

Figure 8:
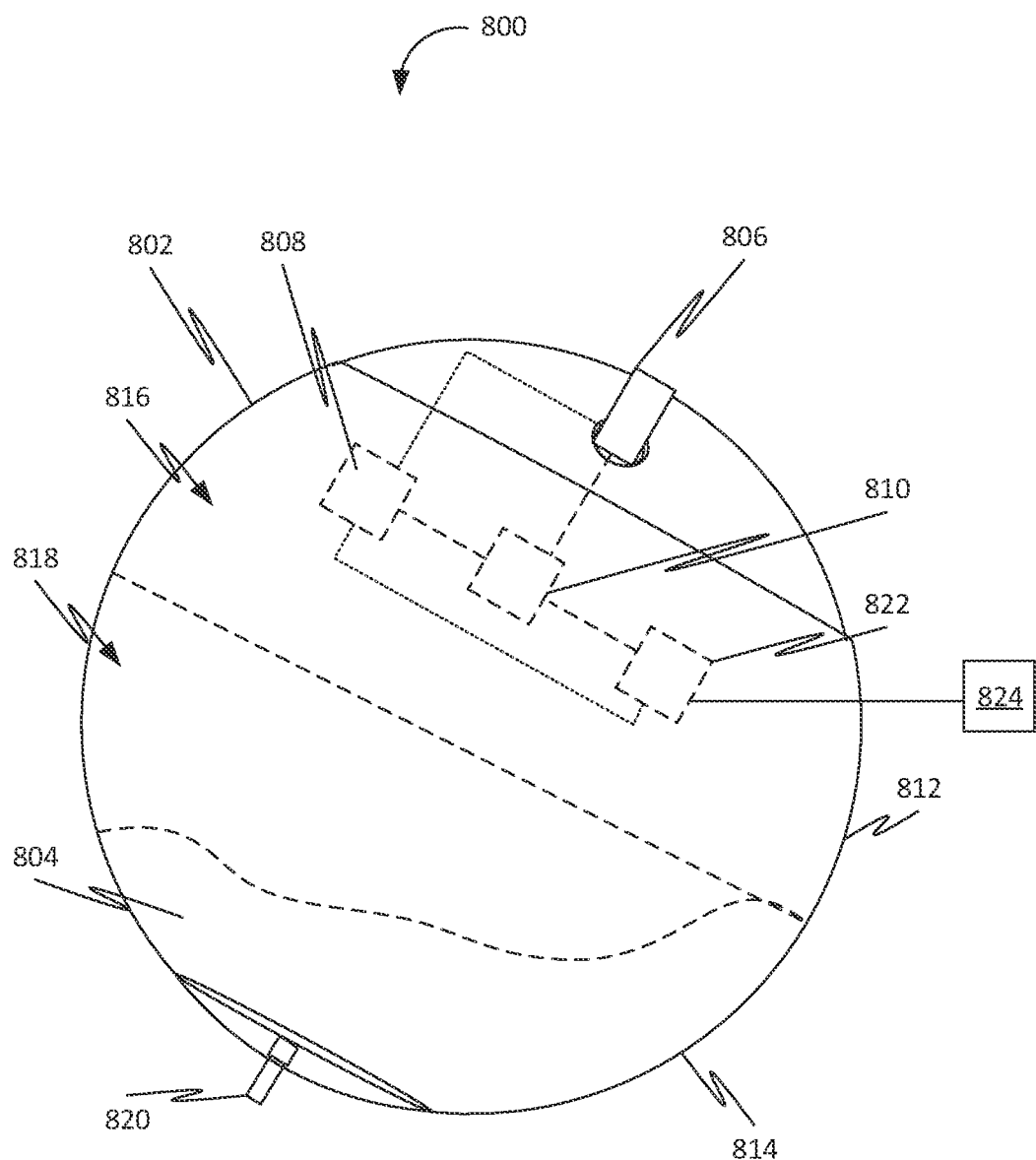
FIG. 8 is a front view of a self deployable apparatus for facilitating collecting data from multiple depths of water bodies, in accordance with some embodiments.

FIG. 8 is a front view of a self deployable apparatus 800 for facilitating collecting data from multiple depths of water bodies, in accordance with some embodiments. Further, the self deployable apparatus 800 may include a main body 802, at least two substances 804, at least one sensor 806, a storage device 808, a communication interface 822, and at least one power source 810.

Further, the main body 802 may include a first body portion 812 and a second body portion 814. Further, the first body portion 812 may include a first interior space 816 and the second body portion 814 may include a second interior space 818. Further, the first interior space 816 may be fluidly isolated from the second interior space 818. Further, the second body portion 814 may include a check valve 820.

Further, the at least two substances 804 in at least two amounts may be disposed in the second interior space 818. Further, the at least two amounts of the at least two substances 804 add at least one weight to the main body 802 for sinking the self deployable apparatus 800 to at least one depth of at least one water body. Further, the at least two amounts of the at least two substances 804 may be configured for undergoing a thermochemical reaction at a temperature for producing at least one gaseous substance in at least one amount. Further, the at least two amounts of the at least two substances 804 achieve the temperature based on the sinking of the self deployable apparatus 800 to the at least one depth of the at least one water body. Further, the at least one amount of the at least one gaseous substance exerts at least one pressure on the check valve 820. Further, the check valve 820 may be configured for expelling at least one portion of the at least one amount of the at least one gaseous substance from the second interior space 818 based on the at least one pressure exerted on the check valve 820. Further, the expelling of the at least one portion of the at least one amount of the at least one gaseous substance from the second interior space 818 corresponds to removing at least one portion of the at least one weight from the main body 802. Further, the removing of the at least one portion of the at least one weight rises the self deployable apparatus 800 to a surface of the at least one water body.

Further, the at least one sensor 806 may be attached to the first body portion 812. Further, the at least one sensor 806 may be configured for generating at least one sensor data based on detecting at least one parameter of at least one water sample in the at least one depth of the at least one water body.

Further, the storage device 808 may be disposed in the first interior space 816. Further, the storage device 808 may be communicatively coupled with the at least one sensor 806. Further, the storage device 808 may be configured for storing the at least one sensor data.

Further, the communication interface 822 may be disposed in the first interior space 816. Further, the communication interface 822 may be communicatively coupled with the storage device 808. Further, the communication interface 822 may be configured for transmitting the at least one sensor 806 data to at least one device 824.

Further, the at least one power source 810 may be disposed in the first interior space 816. Further, the at least one power source 810 may be electrically coupled with the at least one sensor 806, the storage device 808, and the communication interface 822. Further, the at least one power source 810 may be configured for powering the at least one sensor 806, the storage device 808, and the communication interface 822.

Further, in some embodiments, the main body 802 may be spherically shaped.

Further, in some embodiments, the main body 802 may be comprised of at least one material. Further, the at least one material makes the main body 802 lighter than water allowing the main body 802 to float on the surface of the at least one water body. Further, disposing of the at least two amounts of the at least two substances 804 in the second interior space 818 makes the main body 802 denser than the water allowing the main body 802 to sink in the at least one water body.

Further, in some embodiments, the at least two substances 804 comprise at least two aqueous solutions of at least two reactants. Further, the at least two aqueous solutions of the at least two reactants may be associated with at least two concentrations. Further, the at least two concentrations correspond to the temperature for the thermochemical reaction of the at least two amounts of the at least two substances 804. Further, the temperature corresponds to the sinking of the self deployable apparatus 800 to the at least one depth. Further, the at least two concentrations correspond to the sinking of the self deployable apparatus 800 to the at least one depth.

Further, in some embodiments, the at least two substances 804 comprise at least two aqueous solutions of at least two reactants. Further, the at least two aqueous solutions of the at least two reactants may be associated with at least two concentrations. Further, the at least two concentrations correspond the at least one amount of the at least gaseous substance.

Further, in some embodiments, the at least two substances 804 comprise Ammonium Chloride and Sodium Nitrite. Further, the at least one gaseous substance may include nitrogen gas.

Further, in some embodiments, the second body portion 814 may include a second opening leading into the second interior space 818 and a second cover removably coupled with the second opening. Further, the second cover transitions the second opening between a closed state and at least one open state. Further, the second cover fluidly seals the second body portion 814 in the closed state. Further, the at least two amounts of the at least two substances 804 may be to be disposed in the second interior space 818 through the second opening in the at least one open state.

Further, in some embodiments, the first body portion 812 may include a first opening leading into the first interior space 816 and a first cover removably coupled with the first opening. Further, the first cover transitions the first opening between a closed state and at least one open state. Further, the first cover fluidly seals the second body portion 814 in the closed state. Further, at least one of the storage device 808 and the at least one power source 810 may be disposed in the first interior space 816 through the first opening in the at least one open state.

In further embodiments, the self deployable apparatus 800 may include at least one input device, a processing device, and at least one output device. Further, the at least one input device may be disposed on the main body 802. Further, the at least one input device may be configured for receiving at least one depth indication for deploying the self deployable apparatus 800 to the at least one depth. Further, the processing device may be disposed in the first interior space 816. Further, the processing device may be communicatively coupled with the at least one input device. Further, the processing device may be configured for analyzing the at least one depth indication. Further, the processing device may be configured for determining the at least two amounts of the at least two substances 804 based on the analyzing. Further, the processing device may be configured for generating at least one indication of the at least two amounts of the at least two substances 804 based on the determining. Further, the at least one output device may be disposed on the main body 802. Further, the at least one output device may be communicatively coupled with the processing device. Further, the at least one output device may be configured for outputting the at least one indication of the at least two amounts of the at least two substances 804. Further, the at least one power source 810 may be electrically coupled with the at least one input device, the processing device, and the at least one output device. Further, the at least one power source 810 may be further configured for powering the at least one input device, the processing device, and the at least one output device.

Figure 9:
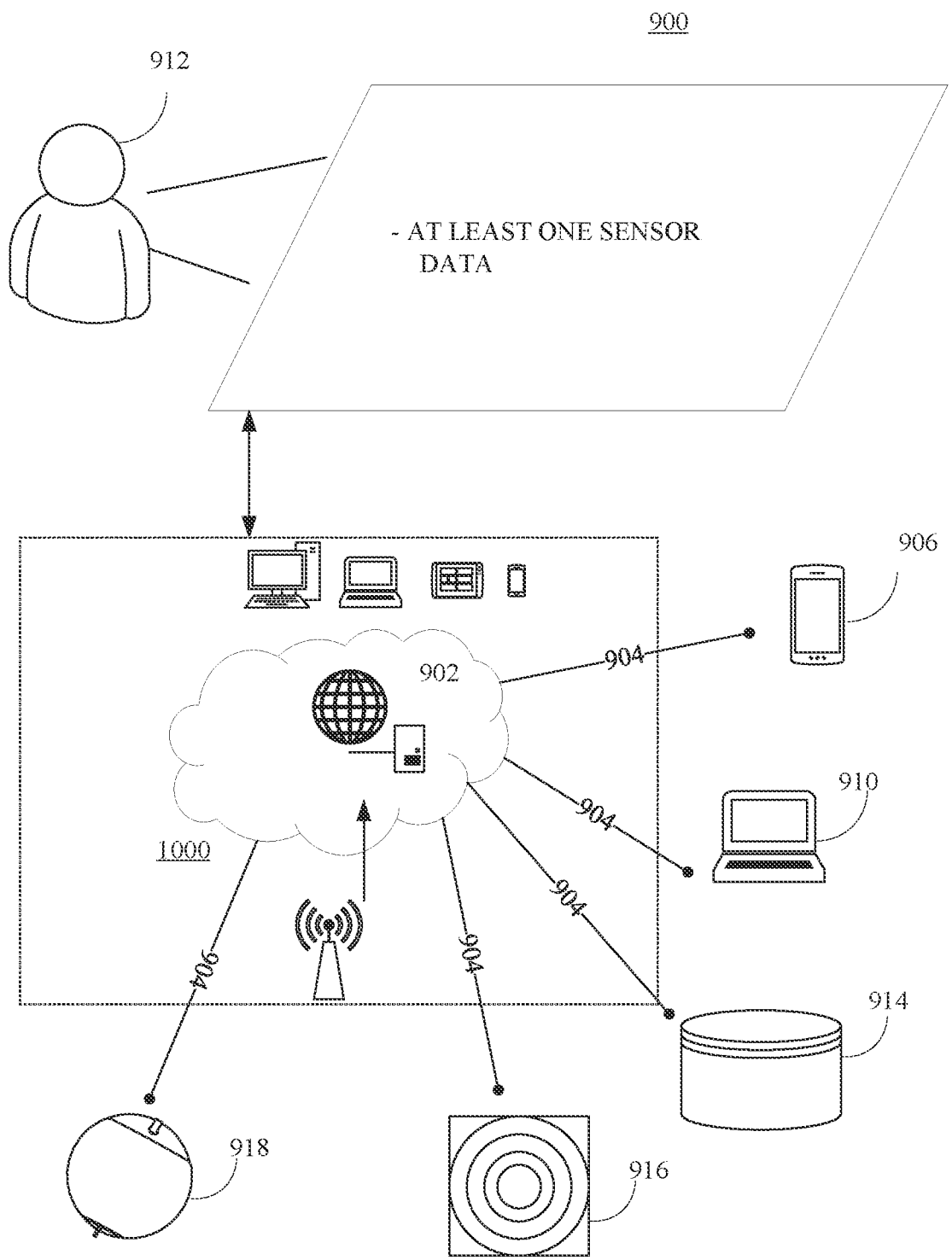
FIG. 9 is an illustration of an online platform consistent with various embodiments of the present disclosure.

FIG. 9 is an illustration of an online platform 900 consistent with various embodiments of the present disclosure. By way of non-limiting example, the online platform 900 to facilitate collecting data from multiple depths of water bodies may be hosted on a centralized server 902, such as, for example, a cloud computing service. The centralized server 902 may communicate with other network entities, such as, for example, a mobile device 906 (such as a smartphone, a laptop, a tablet computer, etc.), other electronic devices 910 (such as desktop computers, server computers, etc.), databases 914, sensors 916, and an apparatus 918 (such as the self deployable apparatus 100, the self deployable apparatus 600, the self deployable apparatus 800, etc.) over a communication network 904, such as, but not limited to, the Internet. Further, users of the online platform 900 may include relevant parties such as, but not limited to, end-users, administrators, service providers, service consumers, and so on. Accordingly, in some instances, electronic devices operated by the one or more relevant parties may be in communication with the platform.

A user 912, such as the one or more relevant parties, may access online platform 900 through a web based software application or browser. The web based software application may be embodied as, for example, but not be limited to, a website, a web application, a desktop application, and a mobile application compatible with a computing device 1000.

Figure 10:
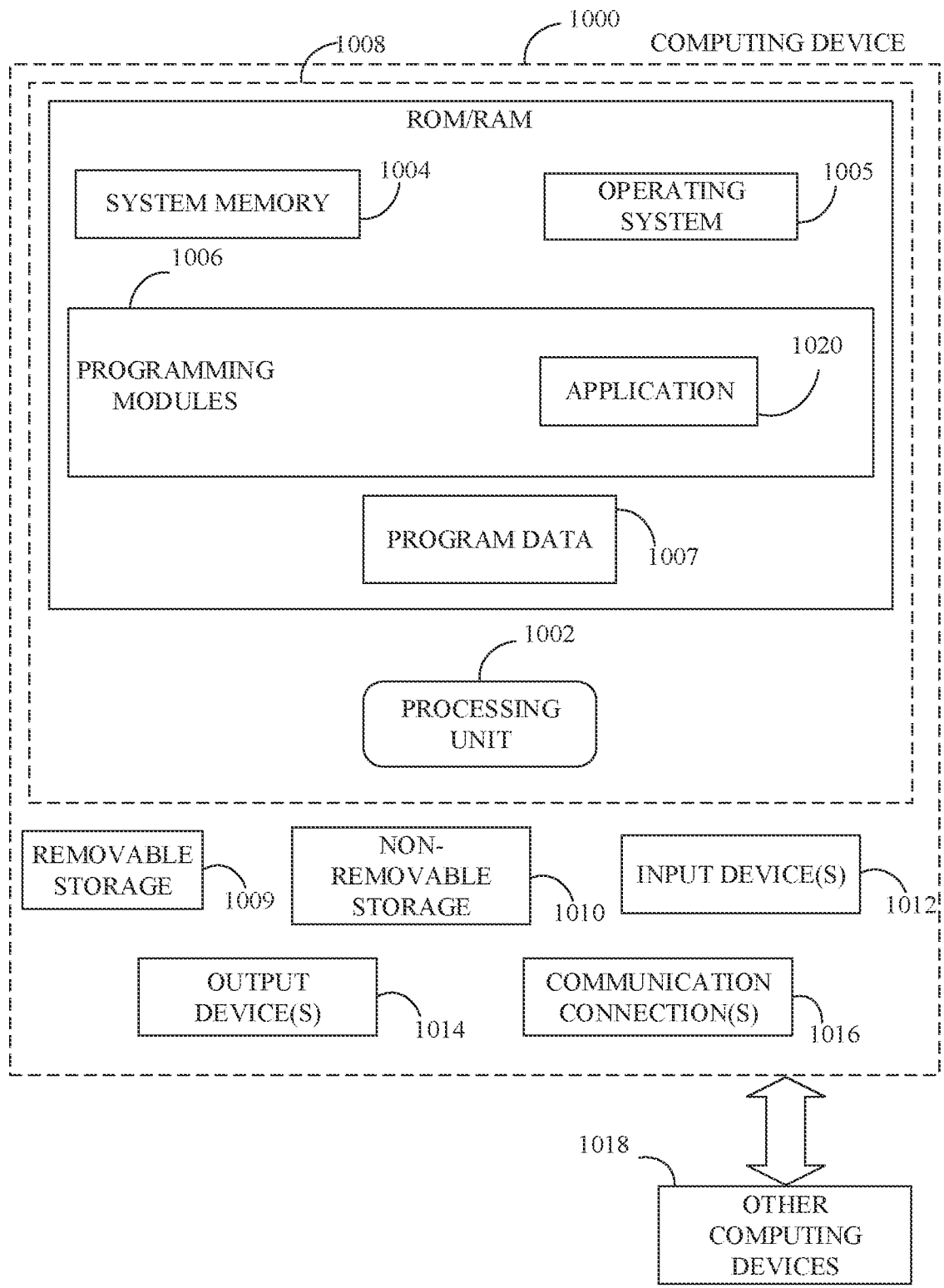
FIG. 10 is a block diagram of a computing device for implementing the methods disclosed herein, in accordance with some embodiments.

With reference to FIG. 10, a system consistent with an embodiment of the disclosure may include a computing device or cloud service, such as computing device 1000. In a basic configuration, computing device 1000 may include at least one processing unit 1002 and a system memory 1004. Depending on the configuration and type of computing device, system memory 1004 may comprise, but is not limited to, volatile (e.g. random-access memory (RAM)), non-volatile (e.g. read-only memory (ROM)), flash memory, or any combination. System memory 1004 may include operating system 1005, one or more programming modules 1006, and may include a program data 1007. Operating system 1005, for example, may be suitable for controlling computing device 1000's operation. Furthermore, embodiments of the disclosure may be practiced in conjunction with a graphics library, other operating systems, or any other application program and is not limited to any particular application or system. This basic configuration is illustrated in FIG. 10 by those components within a dashed line 1008.

Computing device 1000 may have additional features or functionality. For example, computing device 1000 may also include additional data storage devices (removable and/or non-removable) such as, for example, magnetic disks, optical disks, or tape. Such additional storage is illustrated in FIG. 10 by a removable storage 1009 and a non-removable storage 1010. Computer storage media may include volatile and non-volatile, removable and non-removable media implemented in any method or technology for storage of information, such as computer-readable instructions, data structures, program modules, or other data. System memory 1004, removable storage 1009, and non-removable storage 1010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1000. Any such computer storage media may be part of device 1000. Computing device 1000 may also have input device(s) 1012 such as a keyboard, a mouse, a pen, a sound input device, a touch input device, a location sensor, a camera, a biometric sensor, etc. Output device(s) 1014 such as a display, speakers, a printer, etc. may also be included. The aforementioned devices are examples and others may be used.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1004, including operating system 1005. While executing on processing unit 1002, programming modules 1006 (e.g., application 1020 such as a media player) may perform processes including, for example, one or more stages of methods, algorithms, systems, applications, servers, databases as described above. The aforementioned process is an example, and processing unit 1002 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. A self deployable apparatus for facilitating collecting data from multiple depths of water bodies, the self deployable apparatus comprising:

a main body comprising a first body portion and a second body portion, wherein the first body portion comprises a first interior space and the second body portion comprises a second interior space, wherein the first interior space is fluidly isolated from the second interior space, wherein the second body portion comprises a check valve;

at least two substances in at least two amounts are to be disposed in the second interior space, wherein the at least two amounts of the at least two substances add at least one weight to the main body for sinking the self deployable apparatus to at least one depth of at least one water body, wherein the at least two amounts of the at least two substances are configured for undergoing a thermochemical reaction at a temperature for producing at least one gaseous substance in at least one amount, wherein the at least two amounts of the at least two substances achieve the temperature based on the sinking of the self deployable apparatus to the at least one depth of the at least one water body, wherein the at least one amount of the at least one gaseous substance exerts at least one pressure on the check valve, wherein the check valve is configured for expelling at least one portion of the at least one amount of the at least one gaseous substance from the second interior space based on the at least one pressure exerted on the check valve, wherein the expelling of the at least one portion of the at least one amount of the at least one gaseous substance from the second interior space corresponds to removing at least one portion of the at least one weight from the main body, wherein the removing of the at least one portion of the at least one weight rises the self deployable apparatus to a surface of the at least one water body;

at least one sensor attached to the first body portion, wherein the at least one sensor is configured for generating at least one sensor data based on detecting at least one parameter of at least one water sample in the at least one depth of the at least one water body;

a storage device disposed in the first interior space, wherein the storage device is communicatively coupled with the at least one sensor, wherein the storage device is configured for storing the at least one sensor data; and at least one power source disposed in the first interior space, wherein the at least one power source is electrically coupled with the at least one sensor and the storage device, wherein the at least one power source is configured for powering the at least one sensor and the storage device.

2. The self deployable apparatus of claim 1, wherein the main body is spherically shaped.

3. The self deployable apparatus of claim 1, wherein the main body is comprised of at least one material, wherein the at least one material makes the main body lighter than water allowing the main body to float on the surface of the at least one water body, wherein disposing of the at least two amounts of the at least two substances in the second interior space makes the main body denser than the water allowing the main body to sink in the at least one water body.

4. The self deployable apparatus of claim 1, wherein the at least two substances comprise at least two aqueous solutions of at least two reactants, wherein the at least two aqueous solutions of the at least two reactants are associated with at least two concentrations, wherein the at least two concentrations correspond to the temperature for the thermochemical reaction of the at least two amounts of the at least two substances, wherein the temperature corresponds to the sinking of the self deployable apparatus to the at least one depth, wherein the at least two concentrations correspond to the sinking of the self deployable apparatus to the at least one depth.

5. The self deployable apparatus of claim 4 further comprising:
at least one input device disposed on the main body, wherein the at least one input device is configured for receiving at least one depth indication for deploying the self deployable apparatus to the at least one depth;
a processing device disposed in the first interior space, wherein the processing device is communicatively coupled with the at least one input device, wherein the processing device is configured for:
analyzing the at least one depth indication;
determining the at least two concentrations of the at least two reactants based on the analyzing; and
generating at least one indication of the at least two concentrations of the at least two reactants based on the determining; and
at least one output device disposed on the main body, wherein the at least one output device is communicatively coupled with the processing device, wherein the at least one output device is configured for outputting the at least one indication of the at least two concentrations of the at least two reactants, wherein the at least one power source is electrically coupled with the at least one input device, the processing device, and the at least one output device, wherein the at least one power source is further configured for powering the at least one input device, the processing device, and the at least one output device.

6. The self deployable apparatus of claim 1, wherein the at least two substances comprise at least two aqueous solutions of at least two reactants, wherein the at least two aqueous solutions of the at least two reactants are associated with at least two concentrations, wherein the at least two concentrations correspond the at least one amount of the at least gaseous substance.

7. The self deployable apparatus of claim 1, wherein the at least two substances comprise Ammonium Chloride and Sodium Nitrite, wherein the at least one gaseous substance comprises nitrogen gas.

8. The self deployable apparatus of claim 1, wherein the second body portion comprises a second opening leading into the second interior space and a second cover removably coupled with the second opening, wherein the second cover transitions the second opening between a closed state and at least one open state, wherein the second cover fluidly seals the second body portion in the closed state, wherein the at least two amounts of the at least two substances are to be disposed in the second interior space through the second opening in the at least one open state.

9. The self deployable apparatus of claim 1, wherein the first body portion comprises a first opening leading into the first interior space and a first cover removably coupled with the first opening, wherein the first cover transitions the first opening between a closed state and at least one open state, wherein the first cover fluidly seals the second body portion in the closed state, wherein at least one of the storage device and the at least one power source is disposed in the first interior space through the first opening in the at least one open state.

10. The self deployable apparatus of claim 1 further comprising:
at least one input device disposed on the main body, wherein the at least one input device is configured for receiving at least one depth indication for deploying the self deployable apparatus to the at least one depth;
a processing device disposed in the first interior space, wherein the processing device is communicatively coupled with the at least one input device, wherein the processing device is configured for:
analyzing the at least one depth indication;
determining the at least two amounts of the at least two substances based on the analyzing; and
generating at least one indication of the at least two amounts of the at least two substances based on the determining; and
at least one output device disposed on the main body, wherein the at least one output device is communicatively coupled with the processing device, wherein the at least one output device is configured for outputting the at least one indication of the at least two amounts of the at least two substances, wherein the at least one power source is electrically coupled with the at least one input device, the processing device, and the at least one output device, wherein the at least one power source is further configured for powering the at least one input device, the processing device, and the at least one output device.

11. The self deployable apparatus of claim 1 further comprising a communication interface disposed in the first interior space, wherein the communication interface is communicatively coupled with the storage device, wherein the communication interface is configured for transmitting the at least one sensor data to at least one device, wherein the at least one power source is electrically coupled with the communication interface, wherein the at least one power source is configured for powering the communication interface.

12. A self deployable apparatus for facilitating collecting data from multiple depths of water bodies, the self deployable apparatus comprising:
a main body comprising a first body portion and a second body portion, wherein the first body portion comprises a first interior space and the second body portion comprises a second interior space, wherein the first interior space is fluidly isolated from the second interior space, wherein the second body portion comprises a check valve;
at least two substances in at least two amounts are to be disposed in the second interior space, wherein the at least two amounts of the at least two substances add at least one weight to the main body for sinking the self deployable apparatus to at least one depth of at least one water body, wherein the at least two amounts of the at least two substances are configured for undergoing a thermochemical reaction at a temperature for producing at least one gaseous substance in at least one amount, wherein the at least two amounts of the at least two substances achieve the temperature based on the sinking of the self deployable apparatus to the at least one depth of the at least one water body, wherein the at least one amount of the at least one gaseous substance exerts at least one pressure on the check valve, wherein the check valve is configured for expelling at least one portion of the at least one amount of the at least one gaseous substance from the second interior space based on the at least one pressure exerted on the check valve, wherein the expelling of the at least one portion of the at least one amount of the at least one gaseous substance from the second interior space corresponds to removing at least one portion of the at least one weight from the main body, wherein the removing of the at least one portion of the at least one weight rises the self deployable apparatus to a surface of the at least one water body;

at least one sensor attached to the first body portion, wherein the at least one sensor is configured for generating at least one sensor data based on detecting at least one parameter of at least one water sample in the at least one depth of the at least one water body;

a storage device disposed in the first interior space, wherein the storage device is communicatively coupled with the at least one sensor, wherein the storage device is configured for storing the at least one sensor data;

a communication interface disposed in the first interior space, wherein the communication interface is communicatively coupled with the storage device, wherein the communication interface is configured for transmitting the at least one sensor data to at least one device; and at least one power source disposed in the first interior space, wherein the at least one power source is electrically coupled with the at least one sensor, the storage device, and the communication interface, wherein the at least one power source is configured for powering the at least one sensor, the storage device, and the communication interface.

13. The self deployable apparatus of claim 12, wherein the main body is spherically shaped.

14. The self deployable apparatus of claim 12, wherein the main body is comprised of at least one material, wherein the at least one material makes the main body lighter than water allowing the main body to float on the surface of the at least one water body, wherein disposing of the at least two amounts of the at least two substances in the second interior space makes the main body denser than the water allowing the main body to sink in the at least one water body.

15. The self deployable apparatus of claim 12, wherein the at least two substances comprise at least two aqueous solutions of at least two reactants, wherein the at least two aqueous solutions of the at least two reactants are associated with at least two concentrations, wherein the at least two concentrations correspond to the temperature for the thermochemical reaction of the at least two amounts of the at least two substances, wherein the temperature corresponds to the sinking of the self deployable apparatus to the at least one depth, wherein the at least two concentrations correspond to the sinking of the self deployable apparatus to the at least one depth.

16. The self deployable apparatus of claim 12, wherein the at least two substances comprise at least two aqueous solutions of at least two reactants, wherein the at least two aqueous solutions of the at least two reactants are associated with at least two concentrations, wherein the at least two concentrations correspond the at least one amount of the at least gaseous substance.

17. The self deployable apparatus of claim 12, wherein the at least two substances comprise Ammonium Chloride and Sodium Nitrite, wherein the at least one gaseous substance comprises nitrogen gas.

18. The self deployable apparatus of claim 12, wherein the second body portion comprises a second opening leading into the second interior space and a second cover removably coupled with the second opening, wherein the second cover transitions the second opening between a closed state and at least one open state, wherein the second cover fluidly seals the second body portion in the closed state, wherein the at least two amounts of the at least two substances are to be disposed in the second interior space through the second opening in the at least one open state.

19. The self deployable apparatus of claim 12, wherein the first body portion comprises a first opening leading into the first interior space and a first cover removably coupled with the first opening, wherein the first cover transitions the first opening between a closed state and at least one open state, wherein the first cover fluidly seals the second body portion in the closed state, wherein at least one of the storage device and the at least one power source is disposed in the first interior space through the first opening in the at least one open state.

20. The self deployable apparatus of claim 12 further comprising:

at least one input device disposed on the main body, wherein the at least one input device is configured for receiving at least one depth indication for deploying the self deployable apparatus to the at least one depth;

a processing device disposed in the first interior space, wherein the processing device is communicatively coupled with the at least one input device, wherein the processing device is configured for:

analyzing the at least one depth indication;

determining the at least two amounts of the at least two substances based on the analyzing; and generating at least one indication of the at least two amounts of the at least two substances based on the determining; and at least one output device disposed on the main body, wherein the at least one output device is communicatively coupled with the processing device, wherein the at least one output device is configured for outputting the at least one indication of the at least two amounts of the at least two substances, wherein the at least one power source is electrically coupled with the at least one input device, the processing device, and the at least one output device, wherein the at least one power source is further configured for powering the at least one input device, the processing device, and the at least one output device.

* * * * *